US012697102B2

(12) United States Patent
Berrigan et al.

(10) Patent No.: US 12,697,102 B2
(45) Date of Patent: Aug. 4, 2026

(54) SAMPLE COLLECTION DEVICE AND SYSTEM

(71) Applicant: 3M INNOVATIVE PROPERTIES COMPANY, St. Paul, MN (US)

(72) Inventors: Michael R. Berrigan, Oakdale, MN (US); Alan R. Dombrowski, Woodbury, MN (US); Laura R. Nereng, Woodbury, MN (US); Audrey A. Sherman, Woodbury, MN (US); Brett J. Sitter, Marine on St. Croix, MN (US); Narina Y. Stepanova, Woodbury, MN (US); Michael C. Wohl, Bethesda, MD (US)

(73) Assignee: 3M Innovative Properties Company, St. Paul, MN (US)

( * ) Notice: Subject to any disclaimer, the term of this patent is extended or adjusted under 35 U.S.C. 154(b) by 326 days.

(21) Appl. No.: 18/264,779

(22) PCT Filed: Feb. 11, 2022

(86) PCT No.: PCT/IB2022/051250
§ 371 (c)(1),
(2) Date: Aug. 9, 2023

(87) PCT Pub. No.: WO2022/172222
PCT Pub. Date: Aug. 18, 2022

(65) Prior Publication Data
US 2024/0115246 A1    Apr. 11, 2024

Related U.S. Application Data

(60) Provisional application No. 63/227,498, filed on Jul. 30, 2021, provisional application No. 63/200,058, filed on Feb. 12, 2021.

(51) Int. Cl.
| | | |
|---|---|---|
| *A61B 10/00* | (2006.01) | |
| *G01N 33/497* | (2006.01) | |

(52) U.S. Cl.
CPC ........... *A61B 10/00* (2013.01); *G01N 33/497* (2013.01); *A61B 2010/0087* (2013.01)

(58) Field of Classification Search
None
See application file for complete search history.

(56) References Cited

U.S. PATENT DOCUMENTS

| | | | |
|---|---|---|---|
| 6,265,221 | B1 | 7/2001 | Nilsson |
| 6,372,514 | B1 | 4/2002 | Lee |

(Continued)

FOREIGN PATENT DOCUMENTS

| | | |
|---|---|---|
| CA | 2966215 A1 | 5/2016 |
| CN | 1300581 C | 2/2007 |

(Continued)

OTHER PUBLICATIONS

"Filtrete™ Smart MPR 1900 Premium Allergen, Bacteria & Virus Air Filters", 3M Filtrete, 2023, pp. 1-11.

(Continued)

*Primary Examiner* — Jay B Shah
(74) *Attorney, Agent, or Firm* — Ann K. Gallagher

(57) ABSTRACT

A sample collection device including a housing extending from a mouthpiece portion to an air outlet portion. The housing defines an airflow channel from the mouthpiece portion to the air outlet portion. The mouthpiece portion is configured to receive an exhalation airflow. A porous sample collection media is disposed within the housing and along the airflow channel. A fluid inlet port defines an aperture through the housing and is adjacent to the porous sample collection media. The fluid inlet port is configured to direct fluid onto the porous sample collection media. A metered (Continued)

fluid dose element is attached to the fluid inlet port. The metered fluid dose element is configured to dispense a metered volume of fluid into the fluid inlet port.

19 Claims, 7 Drawing Sheets

(56)                    References Cited

U.S. PATENT DOCUMENTS

| | | | |
|---|---|---|---|
| 6,723,056 | B1 | 4/2004 | Alving et al. |
| 7,947,142 | B2 | 5/2011 | Fox et al. |
| 8,162,153 | B2 | 4/2012 | Fox et al. |
| 9,139,940 | B2 | 9/2015 | Berrigan et al. |
| 9,557,329 | B2 | 1/2017 | Lee |
| 9,907,617 | B2 | 3/2018 | Rogers |
| 10,166,381 | B2 | 1/2019 | Gardner et al. |
| 10,273,612 | B2 | 4/2019 | Song et al. |
| 10,359,417 | B2 | 7/2019 | Hammarlund et al. |
| 10,520,439 | B2 | 12/2019 | Palmskog et al. |
| 10,589,277 | B2 | 3/2020 | Ahmad et al. |
| 10,591,460 | B1 | 3/2020 | Ahmad et al. |
| 10,617,780 | B2 | 4/2020 | Dombrowski et al. |
| 10,954,573 | B2 | 3/2021 | Henderson et al. |
| 2007/0144922 | A1 | 6/2007 | Imoarai et al. |
| 2007/0199567 | A1 | 8/2007 | Kanzer |
| 2009/0111088 | A1 | 4/2009 | Martin et al. |
| 2009/0277451 | A1 | 11/2009 | Weinberg |
| 2010/0087749 | A1 | 4/2010 | Tovey |
| 2014/0180156 | A1 | 6/2014 | Ku et al. |
| 2015/0377748 | A1 | 12/2015 | Cooper et al. |
| 2017/0303900 | A1* | 10/2017 | Cardin .................. A61B 10/00 |
| 2019/0346349 | A1 | 11/2019 | Lepene et al. |
| 2020/0245898 | A1 | 8/2020 | Heannue et al. |
| 2021/0059560 | A1 | 3/2021 | Allegra et al. |

FOREIGN PATENT DOCUMENTS

| | | | |
|---|---|---|---|
| CN | 202365779 | U | 8/2012 |
| CN | 111337669 | A | 6/2020 |
| CN | 211148670 | U | 7/2020 |
| CN | 211905393 | U | 11/2020 |
| CN | 212008620 | U | 11/2020 |
| CN | 112034166 | A | 12/2020 |
| CN | 111378018 | B | 1/2021 |
| CN | 213041861 | U | 4/2021 |
| DE | 19718924 | A1 | 10/1998 |
| EP | 2098166 | | 9/2009 |
| EP | 3351171 | B1 | 12/2019 |
| WO | 2015166246 | | 11/2015 |
| WO | 2017087366 | A1 | 5/2017 |
| WO | 2019084092 | A1 | 5/2019 |
| WO | 2019178247 | A1 | 9/2019 |
| WO | 2020170169 | A2 | 8/2020 |
| WO | 2020264241 | A2 | 12/2020 |
| WO | 2021046566 | | 3/2021 |
| WO | 2021216386 | A1 | 10/2021 |
| WO | 2022093876 | A1 | 5/2022 |
| WO | 2022208359 | A1 | 10/2022 |
| WO | 2022214884 | A1 | 10/2022 |
| WO | 2022243753 | A1 | 11/2022 |
| WO | 2022243902 | A1 | 11/2022 |
| WO | 2022248992 | A1 | 12/2022 |
| WO | 2022249061 | A1 | 12/2022 |
| WO | 2023073503 | A1 | 5/2023 |

OTHER PUBLICATIONS

Huynh, "A New Method for Sampling and Detection of Exhaled Respiratory Virus Aerosols", Clinical Infectious Diseases, 2008, vol. 46, pp. 93-95.

International Search Report for PCT International Application No. PCT/IB2022/051250, mailed on May 2, 2022, 6 pages.

Shaikh, "Detection of Mycobacterium tuberculosis RNA in bioaerosols from pulmonary tuberculosis patients", International Journal of Infectious Diseases, vol. 86, 2019, pp. 05-11.

* cited by examiner

SAMPLE COLLECTION DEVICE AND SYSTEM

CROSS REFERENCE TO RELATED APPLICATIONS

This application is a national stage filing under 35 U.S.C. 371 of PCT/IB2022/051250, filed Feb. 11, 2022, which claims the benefit of U.S. Application No. 63/200,058, filed Feb. 12, 2021, and U.S. 63/227,498, filed Jul. 30, 221, the disclosures of which are incorporated by reference in its/their entirety herein.

The present disclosure relates to a sample collection device and system. The present disclosure relates to a bioaerosol collection device and system.

BACKGROUND

Diagnostic tests used to test for the presence of a virus or other pathogen in the airways, throat, or nasopharynx typically involve the insertion of a swab into the back of the nasal passage, the mid-turbinate area of the nasal passage, the anterior nares, or the throat to obtain a sample. The swab is then inserted into a container and analyzed or sent to a lab for processing. Other diagnostic tests involve collecting a saliva sample and then placing it in a container. Currently available at-home viral tests (e.g., COVID-19 tests) involve a nasal swab and a test kit (for example, the Ellume™ test, the Abbot™ BinaxNOW™ test, and the Lucira™ All-in-One test kit). Tests that utilize nasal swab samples or saliva contend with contaminants that can interfere with the various diagnostic tests. As a result, these sample types require a purification step when using RT-PCR molecular testing.

SUMMARY

There is a need for an inexpensive, simple to use, and reliable sample collection device that may be used by laypeople around the world to test to see if they are shedding pathogens or virus. This sample collection device may be paired with a testing device to determine the presence or absence of pathogen or virus in the collected sample.

The sample collection device includes a porous sample collection media disposed within a device housing and along an airflow channel defined by the device housing. A metered dose of fluid is passed through the porous sample collection media and carries away any pathogen or virus bound to the porous sample collection media. The metered dose of fluid may then be analyzed. The metered dose of fluid may be attached or replaceably attached to the housing and transmit the metered dose of fluid through the device housing and onto the porous sample collection media.

It may be desirable to provide a system that includes both a sample collector device and rapid antigen testing in a single device. The integrated device may advantageously be self-contained and sterile such that (unlike swabs which may be contaminated upon use and then become more contaminated during testing, increasing background noise when testing) the pathogen or virus detection may be more accurate or reliable.

DEFINITIONS

Figures 1, 2, 3:
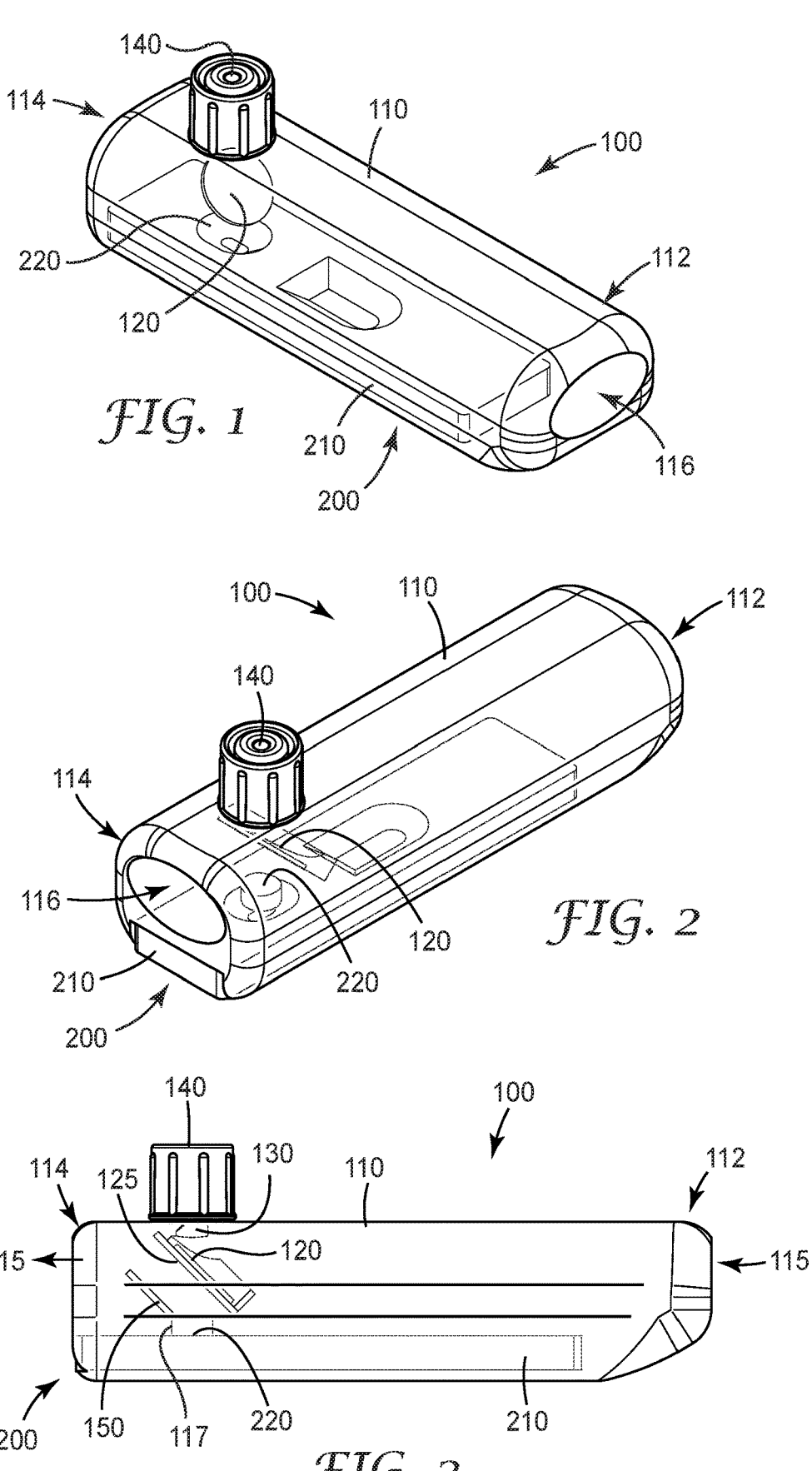
FIG. 1 is a front perspective schematic diagram of an illustrative sample collection device and system.
FIG. 2 is a rear perspective schematic diagram of the sample collection device of FIG. 1.
FIG. 3 is a side elevation schematic diagram of the sample collection device of FIG. 1.

All scientific and technical terms used herein have meanings commonly used in the art unless otherwise specified. The definitions provided herein are to facilitate understanding of certain terms used frequently herein and are not meant to limit the scope of the present disclosure.

The term "substantially" as used here has the same meaning as "significantly," and can be understood to modify the term that follows by at least about 90%, at least about 95%, or at least about 98%. The term "not substantially" as used here has the same meaning as "not significantly," and can be understood to have the inverse meaning of "substantially," i.e., modifying the term that follows by not more than 10%, not more than 5%, or not more than 2%.

The term "about" is used here in conjunction with numeric values to include normal variations in measurements as expected by persons skilled in the art and is understood have the same meaning as "approximately" and to cover a typical margin of error, such as ±5% of the stated value.

Terms such as "a," "an," and "the" are not intended to refer to only a singular entity but include the general class of which a specific example may be used for illustration.

The terms "a," "an," and "the" are used interchangeably with the term "at least one." The phrases "at least one of" and "comprises at least one of" followed by a list refers to any one of the items in the list and any combination of two or more items in the list.

As used here, the term "or" is generally employed in its usual sense including "and/or" unless the content clearly dictates otherwise. The term "and/or" means one or all of the listed elements or a combination of any two or more of the listed elements.

The recitations of numerical ranges by endpoints include all numbers subsumed within that range (e.g., 1 to 5 includes 1, 1.5, 2, 2.75, 3, 3.80, 4, 5, etc. or 10 or less includes 10, 9.4, 7.6, 5, 4.3, 2.9, 1.62, 0.3, etc.). Where a range of values is "up to" or "at least" a particular value, that value is included within the range.

As used here, "have", "having", "include", "including", "comprise", "comprising" or the like are used in their open-ended sense, and generally mean "including, but not limited to." It will be understood that "consisting essentially of," "consisting of," and the like are subsumed in "comprising" and the like. As used herein, "consisting essentially of," as it relates to a composition, product, method or the like, means that the components of the composition, product, method or the like are limited to the enumerated components and any other components that do not materially affect the basic and novel characteristic(s) of the composition, product, method or the like.

The words "preferred" and "preferably" refer to embodiments that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the disclosure, including the claims.

Any direction referred to here, such as "front," "back," "top," "bottom," "left," "right," "upper," "lower," and other directions and orientations are described herein for clarity in reference to the figures and are not to be limiting of an actual device or system or use of the device or system. Devices or systems as described herein may be used in a number of directions and orientations.

The terms "downstream" and "upstream" refer to a relative position based on a direction of exhalation airflow through the device. For example, the upstream-most element of the device is the mouthpiece element, and the downstream-most element of the device is the exhalation outlet element.

DETAILED DESCRIPTION

The present disclosure relates to a sample collection device and system. The present disclosure relates to a bioaerosol collection device and system.

The sample collection device includes a porous sample collection media disposed within a device housing and along an airflow channel defined by the device housing. A metered dose of fluid is passed through the porous sample collection media and carries away pathogen or virus that may be bound to the porous sample collection media. The metered dose of fluid may then be analyzed. The metered dose of fluid may be attached to the housing and transmit the metered dose of fluid through the device housing and onto the porous sample collection media.

In particular, the present disclosure relates to a sample collection device including a housing extending from a mouthpiece or exhalation receipt portion to an air outlet portion. The housing defines an airflow channel from the mouthpiece portion to the air outlet portion. The mouthpiece or exhalation receipt portion is configured to receive an exhalation airflow from one or more of the mouth or nose. For example, the mouthpiece or exhalation receipt portion can be breathed into by contact with the mouth or by contact with the nose/nostril or by contact with each individually or collectively. The exhalation airflow received by the mouthpiece or exhalation receipt portion can be one or both of oral exhalation or nasal exhalation. The term "mouthpiece"

where used herein is meant to refer to an exhalation receipt portion that can receive oral or nasal exhalation of aerosol.

A porous sample collection media is disposed within the housing and along the airflow channel. A fluid inlet port defines an aperture through the housing and is adjacent to the porous sample collection media. The fluid inlet port is configured to direct fluid onto the porous sample collection media. A metered fluid dose element is attached to the fluid inlet port. The metered fluid dose element is configured to dispense a metered volume of fluid into the fluid inlet port.

The porous sample collection media may be disposed or fixed along the airflow channel. The porous sample collection media may be replaceable and changed out by the user, as desired. For example, the user may exhale into the sample collection device and load the porous sample collection media with a sample of the exhalation airflow to form a loaded porous sample collection media. The user may then test the loaded porous sample collection media. The testing may take place with the loaded porous sample collection media in place in the sample collection device, or the user may remove the loaded porous sample collection media from the sample collection device for testing. Then the user may replace the loaded porous sample collection media with an unloaded porous sample collection media into the sample collection device. While the porous sample collection media is illustrated herein as defining a planar element, it is understood that the porous sample collection media may define any shape when disposed within the housing and along the airflow channel.

The metered fluid dose element may be attached to the fluid inlet port. The metered fluid dose element may be permanently attached to the fluid inlet port. In some embodiments, the metered fluid dose element may be integral with the fluid inlet port. The metered fluid dose element may be removably attached to the fluid inlet port. In some embodiments, the metered fluid dose element may be a replaceable element onto the fluid inlet port.

The metered fluid dose element may extend orthogonally from the housing as shown in FIG. 1 to FIG. 10. Alternatively, the metered fluid dose element may extend from the housing at any angle.

The metered fluid dose element may define any shape. The metered fluid dose element may define the shape of a cap or end cap as shown in FIG. 1 to FIG. 10 that discharges fluid from the metered fluid dose element upon movement of the metered fluid dose element towards the housing.

The metered fluid dose element may be deformable and configured to discharges fluid from the metered fluid dose element upon a user squeezing the deformable surface of the metered fluid dose element.

The mouthpiece portion and the air outlet portion may be integral forming a unitary housing. Alternatively, one or both of the mouthpiece portion and the air outlet portion may be separate bodies that may be dismounted from other portions of the housing.

Fluid may be deployed through the fluid inlet port and applied onto the loaded porous sample collection media. The fluid may travel through the surface and thickness of the loaded porous sample collection media and flow off of the porous sample collection media carrying any virus or pathogen that was present on the loaded porous sample collection media. This loaded fluid may then me collected and tested, as described herein.

The sample collection device may include a pressing element that is configured to apply pressure onto the loaded porous sample collection media. This pressing element may force remaining fluid out of the loaded porous sample collection media for collection and testing. The pressing element may be attached to the metered fluid dose element where movement of the metered fluid dose element actuates the pressing element onto the loaded porous sample collection media.

According to an embodiment, a sample collection system includes the sample collection device described above and an assay configured to receive fluid from the fluid collection receptacle.

The assay may be a separate element from the sample collection device. The assay may be configured to attach to the sample collection device. The sample collection device may include a receptable for receiving at least a portion of the assay. The sample collection device may include a receptable for receiving the entire assay. The assay may be a replacement element with the sample collection device.

The assay may be integral with the sample collection device. The assay may form a unitary element with the housing of the sample collection device.

According to another embodiment, a method includes flowing exhalation air through a porous sample collection media. The porous sample collection media is disposed in an airflow channel forming a loaded porous sample collection media. Then flowing a metered dose of fluid through the loaded porous sample collection media disposed in the airflow channel forming an eluent and collecting the eluent. Then the eluent may be tested with an assay.

FIG. 1 shows a front perspective schematic diagram of an illustrative sample collection device 100 and system 200. The housing 110 in these figures is transparent for illustrative proposes only. FIG. 2 is a rear perspective schematic diagram of the sample collection device 100 of FIG. 1. FIG. 3 is a side elevation schematic diagram of the sample collection device 100 of FIG. 1.

The sample collection device 100 including a housing 110 extending from a mouthpiece portion 112 to an air outlet portion 114. The housing 110 defines an airflow channel 116 from the mouthpiece portion 112 to the air outlet portion 114. The mouthpiece portion 112 is configured to receive an exhalation airflow 115. A porous sample collection media 120 is disposed within the housing 110 and along the airflow channel 116. A fluid inlet port 130 defines an aperture through the housing 110 and is adjacent to the porous sample collection media 120. The fluid inlet port 130 is configured to direct fluid onto the porous sample collection media 120. A metered fluid dose element 140 is attached to the fluid inlet port 130. The metered fluid dose element 140 is configured to dispense a metered volume of fluid into the fluid inlet port 130.

The housing 110 may be formed of a rigid material, such as plastic. The airflow channel 116 may extend from a mouthpiece portion 112 opening to an air outlet portion 114 having one or more air outlets. A user exhales into the mouthpiece portion 112 opening and the exhalation airflow 115 leaves the sample collection device 100 through the one or more air outlets at the air outlet portion 114. The airflow channel 116 may extend longitudinally along a longitudinal axis of the housing 110 as shown in FIG. 1, FIG. 2, and FIG. 3. Alternately, the airflow channel 116 may extend co-axially along a central longitudinal axis of the housing 110.

The porous sample collection media 120 may be fixed within the housing 110 and along the airflow channel 116. Exhalation airflow 115 passes through the thickness of the porous sample collection media 120. The porous sample collection media 120 at least partially occludes the airflow channel 116. The porous sample collection media 120 may occlude the airflow channel 116. The porous sample collection media 120 may have a major plane that is orthogonal to the direction of the exhalation airflow 115 passing through the thickness of the porous sample collection media 120.

The porous sample collection media 120 is illustrated as having a major plane that forms an angle with the direction of the incident exhalation airflow 115 passing through the thickness of the porous sample collection media 120. This angle may be in a range from about 91 degrees to about 179 degrees, or from about 100 degrees to about 160 degrees, or about 115 degrees to about 150 degrees, or about 125 to about 145 degrees.

The porous sample collection media 120 may be a nonwoven material configured to filter pathogens or virus from an exhalation airflow 115. The porous sample collection media 120 may be a nonwoven material having an electrostatic charge configured to filter pathogens or virus from an exhalation airflow 115. The porous sample collection media 120 may be a hydrophobic nonwoven material configured to filter pathogens or virus from an exhalation airflow 115. The porous sample collection media 120 may be a hydrophobic nonwoven material having an electrostatic charge configured to filter pathogens or virus from an exhalation airflow 115.

The term "hydrophobic" refers to a material having a water contact angle of 90 degrees or greater, or from about 90 degrees to about 170 degrees, or from about 100 degrees to about 150 degrees. Water contact angle is measured using ASTM D5727-1997 Standard test method for surface wettability and absorbency of sheeted material using an automated contact angle tester.

The porous sample collection media 120 may be formed of polymeric material. The porous sample collection media 120 may be formed of a polyolefin. The porous sample collection media 120 may be formed of polypropylene. One illustrative porous sample collection media 120 is commercially available from 3M Company (St. Paul MN, U.S.A.) under the trade designation FILTRETE Smart MPR 1900 Premium Allergen, Bacteria & Virus Air Filter Mew 13.

The porous sample collection media may be formed of a of a polylactide (PLA) such as, for example, 6100D from NatureWorks LLC15305 Minnetonka Blvd Minnetonka, MN 55345. Exemplary nonwoven filtration layer materials for use in or as the porous sample collection media include, for example, those described in U.S. Pat. Nos. 7,947,142; 8,162,153; 9,139,940; and 10,273,612, all of which are incorporated herein in their entirety.

The sample collection media may be pleated. In some embodiments, the pleat frequency is between about 1 pleat per 0.6 cm of media and about 1 pleat per 2 mm of media. In some embodiments, the pleat height is between about 2 mm and about 4 mm.

The porous sample collection media 120 may have a thickness (orthogonal to the major plane) in a range from 200 to 1000 micrometers, or from 250 to 750 micrometers. The porous sample collection media 120 may have major plane surface area in a range from about 1 $cm^2$ to about 4 $cm^2$, or about 2 $cm^2$ to about 3 $cm^2$.

The porous sample collection media 120 may be fixed directly to the housing 110. FIG. 3 shows a support element 125 in contact with and supporting the porous sample collection media 120. The support element 125 includes one or more apertures configured to allow exhalation airflow to pass through the support element 125. The support element 125 may be fixed to the housing 110 and disposed within the airflow channel 116. The porous sample collection media 120 may be fixed directly to the support element 125.

The metered fluid dose element 140 may be attached to the fluid inlet port 130 and movable between a first fluid loaded position and a second fluid depleted position, where the second fluid depleted position may be closer to the housing than the first fluid loaded position. In the first fluid loaded position the metered fluid dose element 140 contains the metered volume of fluid and in the second fluid depleted position the metered fluid dose element 140 delivers the metered volume of fluid into the fluid inlet 130 and onto the porous sample collection media 120. FIG. 3 illustrates the metered fluid dose element 140 in the second fluid depleted position.

The metered fluid dose element 140 may contain a fluid reservoir of fluid. The metered fluid dose element 140 may define a volume configured to retain a fluid reservoir of fluid and release the fluid reservoir of fluid as the metered fluid dose element 140 moved from the first fluid loaded position to the second fluid depleted position. The metered fluid dose element 140 may include a plunger element (described below) that moves into the volume configured to retain a fluid reservoir of fluid and release the fluid reservoir of fluid as the metered fluid dose element 140 moved from the first fluid loaded position to the second fluid depleted position. One illustrative metered fluid dose element 140 is commercially available from 3M Company (St. Paul MN, U.S.A.) under the trade designation CUROS.

The fluid inlet port 130 may define a protrusion extending from an outer surface of the housing 110. The metered fluid dose element 140 may define a cap movably attached to the protrusion between the first fluid loaded position and the second fluid depleted position.

The porous sample collection media 120 defines a major surface area value and the fluid reservoir 142 defines a volume value, and the volume value divided by the surface area value may be in a range from 10 microliters/cm2 to 400 microliter/cm2, or from 10 microliters/cm2 to 250 microliter/cm2, or from 50 microliters/cm2 to 150 microliter/cm2. In some embodiments, the fluid reservoir 142 defines a volume in a range from 50 microliters to 500 microliters.

The metered fluid dose element 140 may be movably attached via a threaded connection with the fluid inlet port 130. Thus, the metered fluid dose element 140 may be moved between the first fluid loaded position and the second fluid depleted position by rotating the metered fluid dose element 140 about a threaded axis.

The fluid dispensed by the metered fluid dose element 140 may be an aqueous fluid. The fluid dispensed by the metered fluid dose element 140 may be an aqueous buffer solution. The fluid dispensed by the metered fluid dose element 140 may be an aqueous fluid with a surfactant. The fluid dispensed by the metered fluid dose element 140 may be saline solution. The fluid dispensed by the metered fluid dose element 140 may be a saline solution comprising a surfactant. The fluid dispensed by the metered fluid dose element 140 may be a saline solution comprising from 0.5% to 2% surfactant by weight.

The sample collection device 100 may further include a fluid flow channel configured to direct fluid from the fluid inlet port 130 to the porous sample collection media 120. The fluid flow channel may deliver fluid via capillary action to the porous sample collection media 120.

The sample collection device 100 may include a fluid collection receptacle 150 disposed within the housing 110 and configured to receive fluid from the porous sample collection media 120. The sample collection device 100 may further include a second fluid flow channel configured to direct fluid from the porous sample collection media 120. The fluid flow channel may deliver fluid via capillary action.

In some embodiments, the sample collection device 100 may include two, three, four, or five, or more fluid inlet ports 130. Each fluid inlet port 130 may independently include a metered fluid dose element 140 movably attached to the corresponding fluid inlet port 130. The two or more metered fluid dose elements 140 may each include the same fluid material. Alternatively, at least one of the two or more metered fluid dose elements 140 may include a fluid material that is different than fluid material contained in another metered fluid dose element 140. For example, the fluid independently chosen for each metered fluid dose element 140 may be chosen to interact, react, activate, de-activate another independently chosen fluid in another metered fluid dose element 140.

The disclosure is also directed to a sample collection system 200. The sample collection system 200 includes the sample collection device 100 described above and an assay 210 configured to receive fluid from the fluid collection receptacle 150. As described above, the assay 210 may be integral with the sample collection device 100 forming a unitary body, or the assay 210 may be a replaceable element received and removed from the housing 110.

The housing 110 may include an aperture configured to receive the assay 210. The housing 110 aperture 117 may mate with the assay 210 and receive at least a portion of the assay within the housing 110 aperture. In one embodiment, the housing 110 aperture may receive the entire assay 210 within the housing.

The assay 210 may include a sample inlet 220. The sample inlet 220 may be registered with the fluid collection receptacle 150. Fluid from the porous sample collection media 120 may flow into the fluid collection receptacle 150 and into the sample inlet 220 of the assay 210.

The assay 210 may be a flow assay, such as a lateral flow assay or a vertical flow assay. The assay 210 may detects a virus or pathogen. The assay 210 may include a test result display window to indicate the presence or absence of a virus or pathogen.

An assay may be referred to as lateral flow assays (LFAs) or vertical flow assays (VFAs) which are, generally, paper-based platforms for the detection and quantification of analytes in complex mixtures, where the sample is placed on a test device and the results are displayed within 5-30 min. Low development costs and ease of production of LFAs have resulted in the expansion of its applications to multiple fields in which rapid tests are required. LFA-based tests are widely used in hospitals, physician's offices and clinical laboratories for the qualitative and quantitative detection of specific antigens and antibodies, as well as products of gene amplification. A variety of biological samples can be tested using assays.

FIG. 1 illustrates the porous sample collection media 120 may be adjacent to the assay 210 sample inlet 220. The porous sample collection media 120 may direct the fluid directly into the sample inlet 220. In some embodiments, the porous sample collection media 120 may be in contact with the sample inlet 220. The porous sample collection media 120 may direct the fluid directly into the sample inlet 220 via capillary action.

Figure 4:
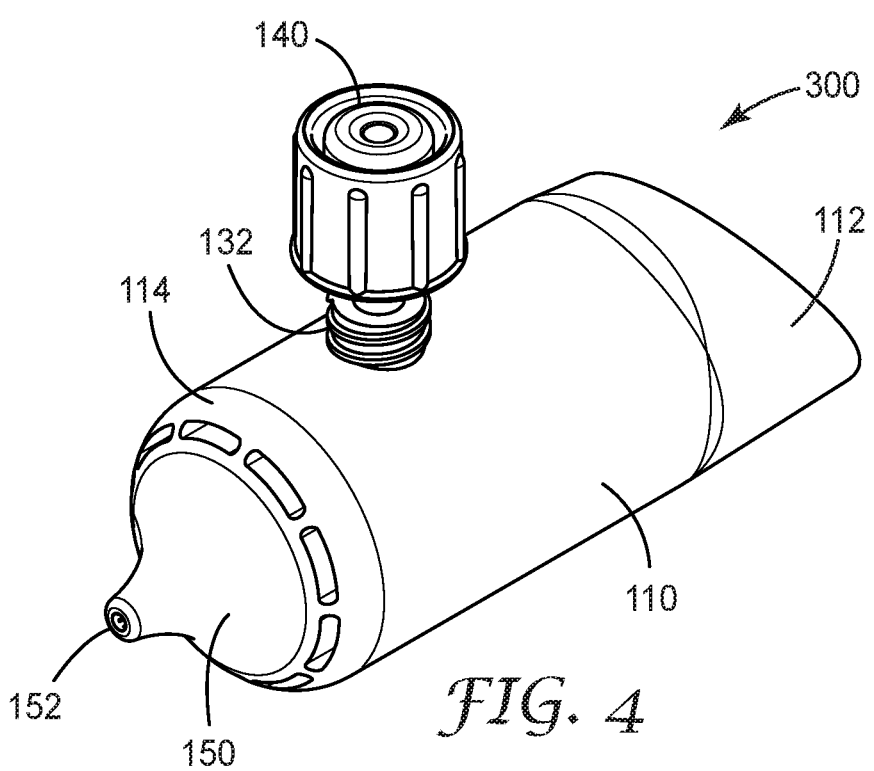
FIG. 4 is a rear perspective schematic diagram of another illustrative sample collection device.
Figure 5:
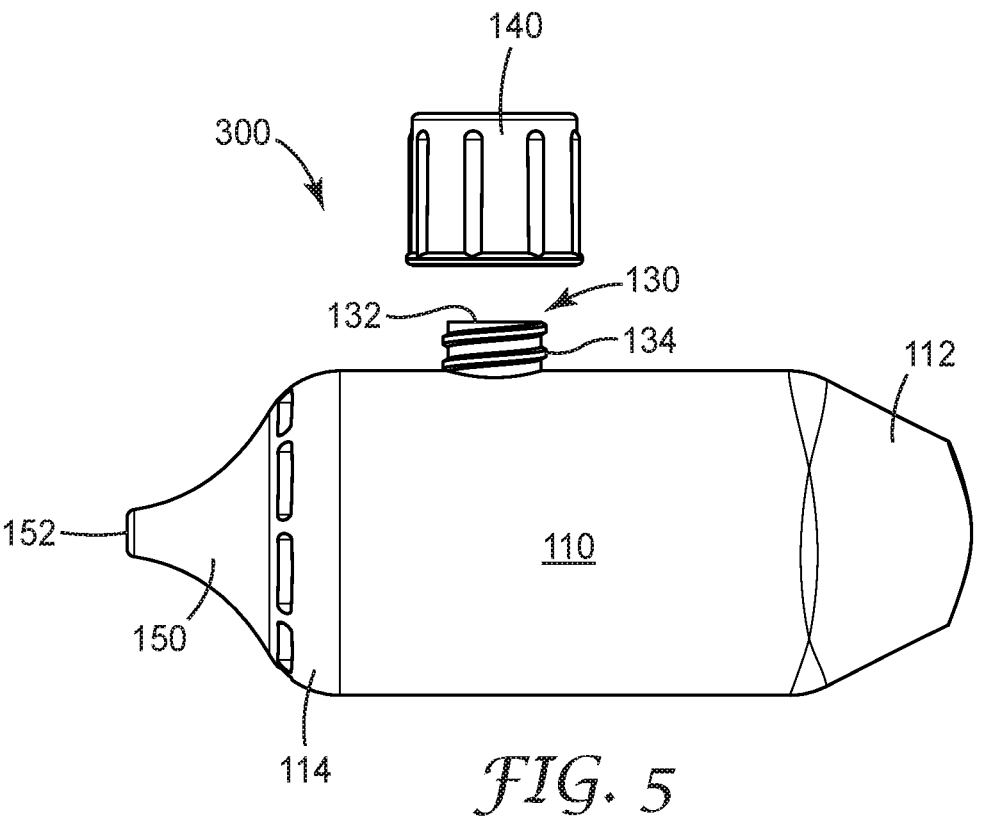
FIG. 5 is a side elevation schematic diagram of the sample collection device of FIG. 4.
Figure 6:
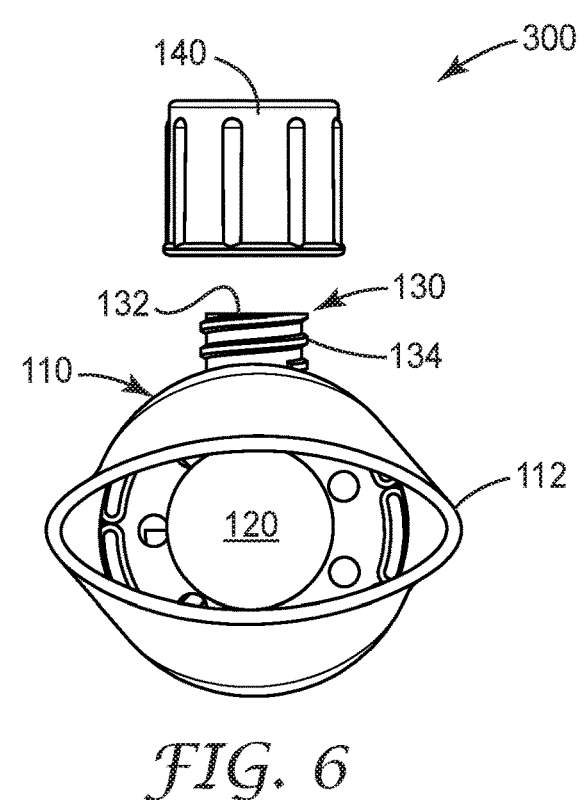
FIG. 6 is a front elevation schematic diagram of the sample collection device of FIG. 4.
Figure 7:
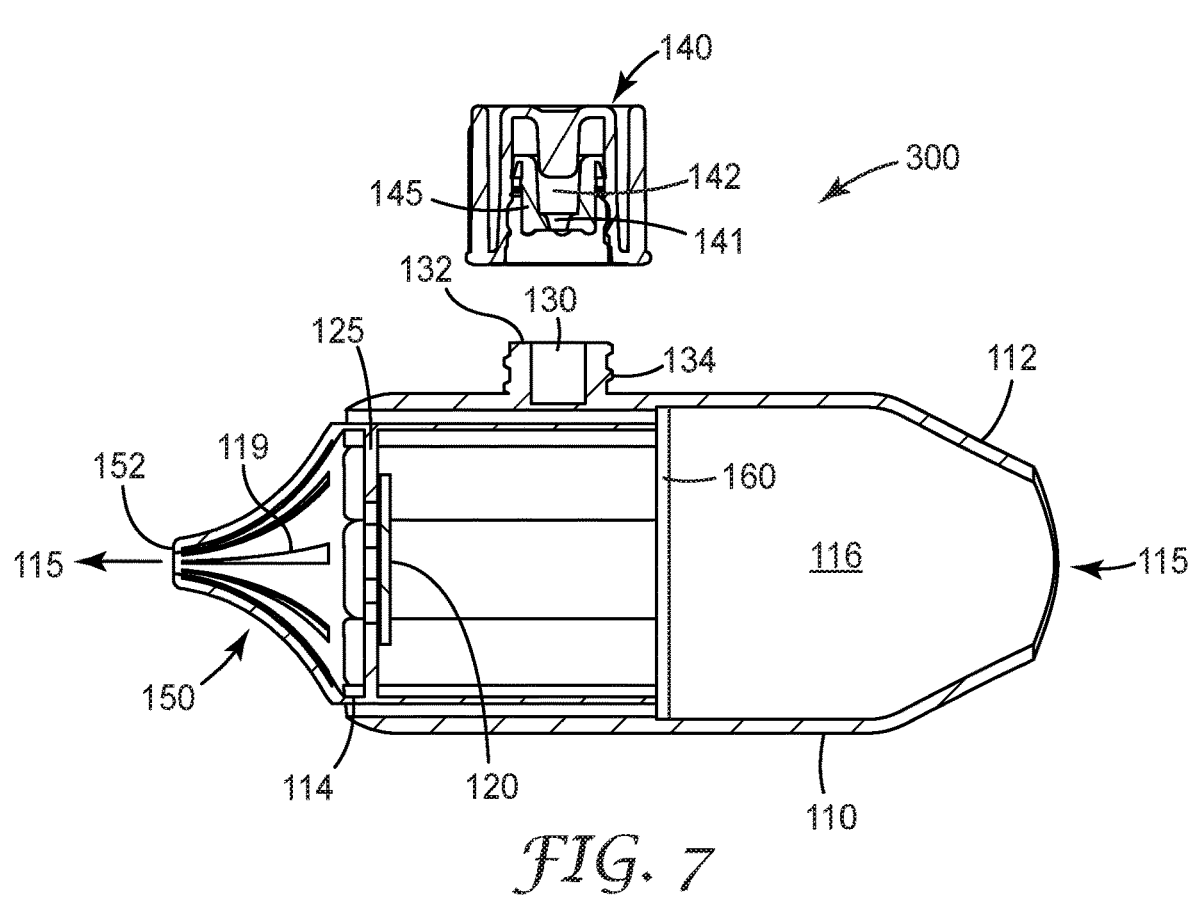
FIG. 7 is a cross-sectional schematic diagram of the sample collection device of FIG. 5.

FIG. 4 is a rear perspective schematic diagram of another illustrative sample collection device 300. FIG. 5 is a side elevation schematic diagram of the sample collection device 300 of FIG. 4. FIG. 6 is a front elevation schematic diagram of the sample collection device 300 of FIG. 4. FIG. 7 is a cross-sectional schematic diagram of the sample collection device 300 of FIG. 5. These Figures illustrate the metered fluid dose element 140 exploded away from the fluid inlet port 130, for clarity.

In this embodiment, air flows through both the porous sample collection media 120 and bypass vents, shown in FIG. 6, surrounding the porous sample collection media 120. The ratio of area of bypass vents to area of porous sample collection media 120 may be altered to get proper airflow through the sample collection device 300 with adequate virus capture onto the porous sample collection media 120.

The sample collection device 300 including a housing 110 extending from a mouthpiece portion 112 to an air outlet portion 114. The housing 110 defines an airflow channel 116 from the mouthpiece portion 112 to the air outlet portion 114. The mouthpiece portion 112 is configured to receive an exhalation airflow 115. A porous sample collection media 120 is disposed within the housing 110 and along the airflow channel 116. A fluid inlet port 130 defines an aperture through the housing 110 and is adjacent to the porous sample collection media 120. The fluid inlet port 130 is configured to direct fluid onto the porous sample collection media 120. A metered fluid dose element 140 is attached to the fluid inlet port 130. The metered fluid dose element 140 is configured to dispense a metered volume of fluid into the fluid inlet port 130.

The housing 110 may be formed of a rigid material, such as plastic. The airflow channel 116 may extend from a mouthpiece portion 112 opening to an air outlet portion 114 having one or more air outlets. A user exhales into the mouthpiece portion 112 opening and the exhalation airflow leaves the sample collection device 300 through the one or more air outlets at the air outlet portion 114. The airflow channel 116 may extend longitudinally along a longitudinal axis of the housing 110. Alternatively, the airflow channel 116 may extend co-axially along a central longitudinal axis of the housing 110.

The porous sample collection media 120 is fixed within the housing 110 and along the airflow channel 116. Exhalation airflow 115 passes through the thickness of the porous sample collection media 120. The porous sample collection media 120 at least partially occludes the airflow channel 116. The porous sample collection media 120 may occlude the airflow channel 116. The porous sample collection media 120 is illustrated as having a major plane that is orthogonal to the direction of the exhalation airflow 115 passing through the thickness of the porous sample collection media 120.

In other embodiments, the porous sample collection media 120 may have a major plane that forms an angle with the direction of the incident exhalation airflow 115 passing through the thickness of the porous sample collection media 120. This angle may be in a range from about 91 degrees to about 179 degrees, or from about 100 degrees to about 160 degrees, or about 115 degrees to about 150 degrees, or about 125 to about 145 degrees.

The porous sample collection media 120 may be a nonwoven material configured to filter pathogens or virus from an exhalation airflow 115. The porous sample collection media 120 may be a nonwoven material having an electrostatic charge configured to filter pathogens or virus from an exhalation airflow 115. The porous sample collection media 120 may be a hydrophobic nonwoven material configured to filter pathogens or virus from an exhalation airflow 115. The porous sample collection media 120 may be a hydrophobic nonwoven material having an electrostatic charge configured to filter pathogens or virus from an exhalation airflow 115.

The porous sample collection media 120 may be formed of any of the materials described herein. The porous sample collection media 120 may be fixed directly to the housing 110. FIG. 7 shows a support element 125 in contact with and supporting the porous sample collection media 120. The support element 125 includes one or more apertures configured to allow exhalation airflow to pass through the support element 125. The support element 125 may be fixed to the housing 110 and disposed within the airflow channel 116. The porous sample collection media 120 may be fixed directly to the support element 125.

The metered fluid dose element 140 may be movably attached to the fluid inlet port 130 between at least a first fluid loaded position and a second fluid depleted position, where the second fluid depleted position is closer to the housing than the first fluid loaded position. In the first fluid loaded position the metered fluid dose element 140 contains the metered volume of fluid and in the second fluid depleted position the metered fluid dose element 140 delivers the metered volume of fluid into the fluid inlet 130 and onto the porous sample collection media 120.

The metered fluid dose element 140 may contain a reservoir of fluid 142. The metered fluid dose element 140 may define a volume configured to retain a reservoir of fluid 142 and release the reservoir of fluid 142 as the metered fluid dose element 140 moved from the first fluid loaded position to the second fluid depleted position. The metered fluid dose element 140 may include a plunger element 145 that moves into the volume configured to retain a reservoir of fluid 142 and release the reservoir of fluid 142 as the metered fluid dose element 140 moved from the first fluid loaded position to the second fluid depleted position. The plunger element 145 that may include an aperture 141 to release the fluid from the reservoir of fluid 142 as the metered fluid dose element 140 moved from the first fluid loaded position to the second fluid depleted position. A seal element may be disposed over the aperture 141 to seal the fluid within reservoir of fluid 142. The seal may be broken by the pressure of the fluid as the metered fluid dose element 140 is moved to the second fluid depleted position. One illustrative metered fluid dose element 140 is commercially available from 3M Company (St. Paul MN, U.S.A.) under the trade designation CUROS. FIG. 7 illustrates to cross-sectional view of the metered fluid dose element 140. The metered fluid dose element 140 shown in FIGS. 1-6 and 8-9 include these elements illustrated here in the cross-sectional of FIG. 7.

The fluid inlet port 130 may define a protrusion 132 extending away from an outer surface of the housing 110. The metered fluid dose element 140 may define a cap movably attached to the protrusion 132 between, at least, the first fluid loaded position and the second fluid depleted position.

The porous sample collection media 120 defines a major surface area value and the fluid reservoir 142 defines a volume value, and the volume value divided by the surface area value may be in a range from 10 microliters/cm2 to 400 microliter/cm2, or from 10 microliters/cm2 to 250 microliter/cm2, or from 50 microliters/cm2 to 150 microliter/cm2. In some embodiments, the fluid reservoir 142 defines a volume in a range from 50 microliters to 500 microliters.

The metered fluid dose element 140 may be movably attached via a threaded connection 134 with the fluid inlet port 130. Thus, the metered fluid dose element 140 may be moved between the first fluid loaded position and the second fluid depleted position by rotating the metered fluid dose element 140 about a threaded axis.

The fluid dispensed by the metered fluid dose element 140 may be any fluid described herein.

The sample collection device 300 may further include a fluid flow channel configured to direct fluid from the fluid inlet port 130 to the porous sample collection media 120. The fluid flow channel may deliver fluid via capillary action to the porous sample collection media 120.

The sample collection device 300 may include a fluid collection receptacle 150 disposed within the housing 110 and configured to receive fluid from the porous sample collection media 120. The sample collection device 300 may further include a second fluid flow channel 119 configured to direct fluid from the porous sample collection media 120. The second fluid flow channel 119 may deliver fluid via capillary action. The fluid collection receptacle 150 may include a fluid outlet 152 configured to direct fluid out of the sample collection device 300.

The sample collection device 300 may include a pre-filter element 160 fixed within the housing 110 and along the airflow channel 116. The pre-filter element 160 may be located between the mouthpiece element 112 and the porous sample collection media 120 along the airflow channel 116. The pre-filter element 160 may be located between the mouthpiece element 112 and the fluid inlet ports 130 along the airflow channel 116. Exhalation airflow 115 passes through the thickness of the pre-filter element 160. The pre-filter element 160 at least partially occludes the airflow channel 116. The pre-filter element 160 may occlude the airflow channel 116.

The pre-filter element 160 is illustrated as having a major plane that is orthogonal to the direction of the exhalation airflow 115 passing through the thickness of the pre-filter element 160. The pre-filter element 160 may be a non-woven layer configured to filter out larger particles from the exhalation airflow 115 passing through the pre-filter element 160. The pre-filter element 160 may be a non-woven layer that does not have an electrostatic charge. The pre-filter element 160 is configured to not capture virus or pathogens. The pre-filter element 160 is configured to allow virus or pathogens to transmit through the pre-filter element 160. The pre-filter element 160 may be incorporated into any of the embodiments illustrated herein.

In some embodiments, the sample collection device 300 may include two, three, four, or five, or more fluid inlet ports 130. Each fluid inlet port 130 may independently include a metered fluid dose element 140 movably attached to the corresponding fluid inlet port 130. The two or more metered fluid dose elements 140 may each include the same fluid material. Alternatively, at least one of the two or more metered fluid dose elements 140 may include a fluid material that is different than fluid material contained in another metered fluid dose element 140. As described above, the different fluids may be chosen to interact or react with each other upon deployment of each fluid into the sample collection device 300.

The disclosure is also directed to a sample collection system, as described above. The sample collection system includes the sample collection device 300 and an assay configured to receive fluid from the fluid collection receptacle 150 via the fluid outlet 152.

Figure 8:
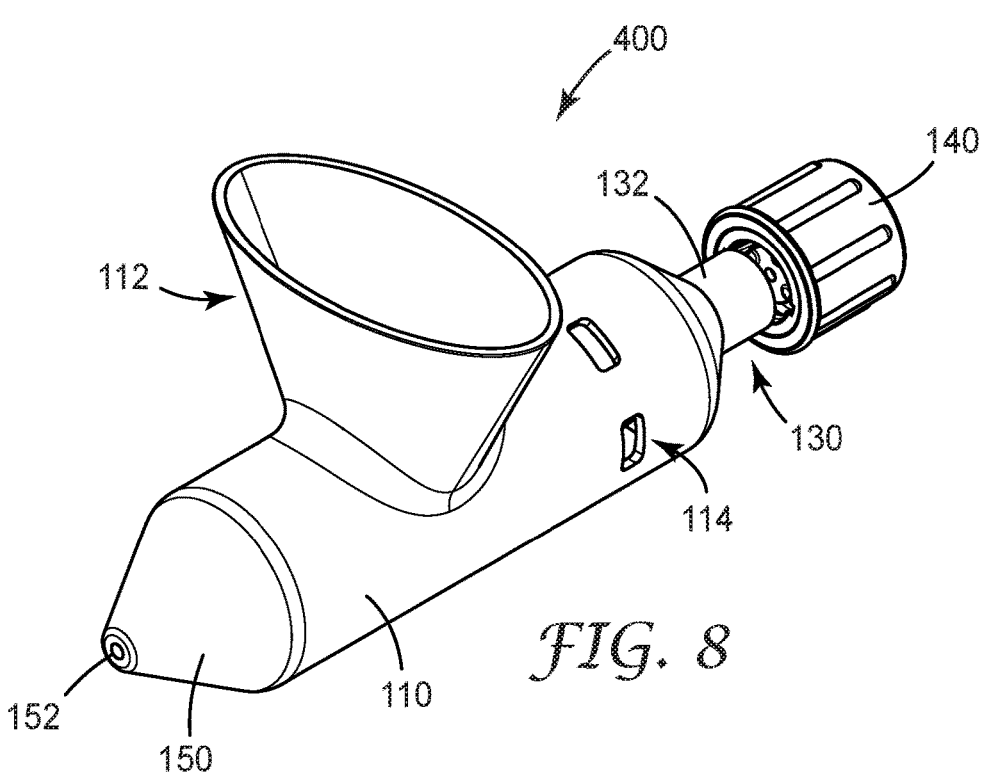
FIG. 8 is a rear perspective schematic diagram of another illustrative sample collection device.
Figure 9:
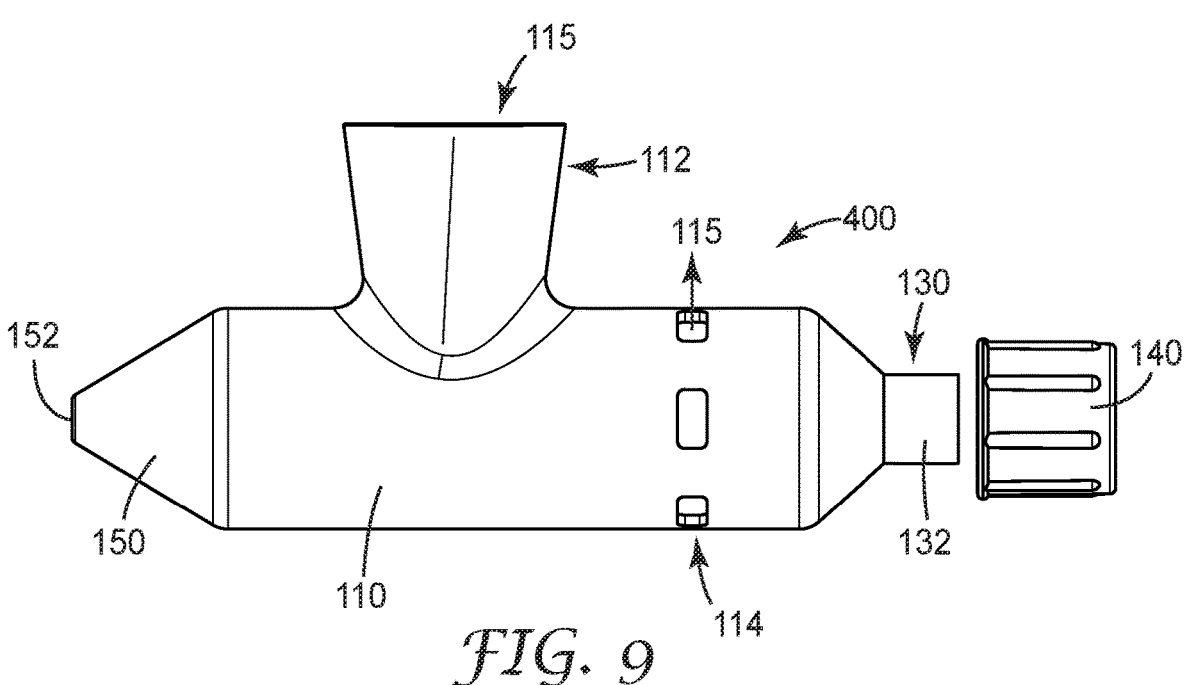
FIG. 9 is a side elevation schematic diagram of the sample collection device of FIG. 8.
Figure 10:
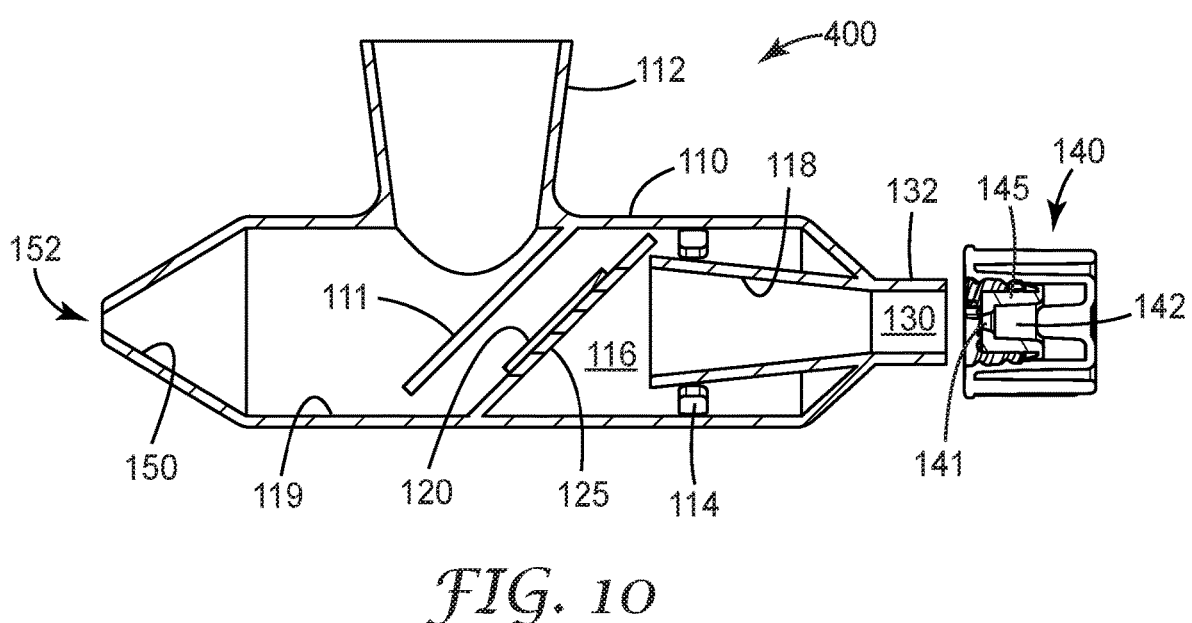
FIG. 10 is a cross-sectional schematic diagram of the sample collection device of FIG. 9.

FIG. 8 is a rear perspective schematic diagram of another illustrative sample collection device 400. FIG. 9 is a side elevation schematic diagram of the sample collection device 400 of FIG. 8. FIG. 10 is a cross-sectional schematic diagram of the sample collection device 400 of FIG. 9. These Figures illustrate the metered fluid dose element 140 exploded away from the fluid inlet port 130, for clarity.

The sample collection device 400 including a housing 110 extending from a mouthpiece portion 112 to an air outlet portion 114. The housing 110 defines an airflow channel 116 from the mouthpiece portion 112 to the air outlet portion 114. The mouthpiece portion 112 is configured to receive an exhalation airflow 115. A porous sample collection media 120 is disposed within the housing 110 and along the airflow channel 116. A fluid inlet port 130 defines an aperture through the housing 110 and is adjacent to the porous sample collection media 120. The fluid inlet port 130 is configured to direct fluid onto the porous sample collection media 120. A metered fluid dose element 140 is movably attached to the fluid inlet port 130. The metered fluid dose element 140 is configured to dispense a metered volume of fluid into the fluid inlet port 130.

The housing 110 may be formed of a rigid material, such as plastic. The airflow channel 116 may extend from a mouthpiece portion 112 opening to an air outlet portion 114 having one or more air outlets. A user exhales into the mouthpiece portion 112 opening and the exhalation airflow leaves the sample collection device 400 through the one or more air outlets at the air outlet portion 114. The airflow channel 116 may extend longitudinally along at least a portion of a longitudinal axis of the housing 110. The airflow channel 116 may extend co-axially along at least a portion of a central longitudinal axis of the housing 110.

The porous sample collection media 120 is disposed within the housing 110 and along the airflow channel 116. Exhalation airflow 115 passes through the thickness of the porous sample collection media 120. The porous sample collection media 120 at least partially occludes the airflow channel 116. The porous sample collection media 120 may occlude the airflow channel 116. The porous sample collection media 120 may have a major plane that is orthogonal to the direction of the exhalation airflow 115 passing through the thickness of the porous sample collection media 120.

The porous sample collection media 120 is shown having a major plane that forms an angle with the direction of the incident exhalation airflow 115 passing through the thickness of the porous sample collection media 120. This angle may be in a range from about 91 degrees to about 179 degrees, or from about 100 degrees to about 160 degrees, or about 115 degrees to about 150 degrees, or about 125 to about 145 degrees.

The porous sample collection media 120 may be formed of any of the materials described above.

The porous sample collection media 120 may be fixed directly to the housing 110. FIG. 10 shows a support element 125 in contact with and supporting the porous sample collection media 120. The support element 125 includes one or more apertures configured to allow exhalation airflow to pass through the support element 125. The support element 125 may be fixed to the housing 110 and disposed within the airflow channel 116. The porous sample collection media 120 may be fixed directly to the support element 125.

A baffle 111 may be fixed directly to the housing 110. The baffle 111 may be fixed to the housing 110 and disposed within the airflow channel 116. The baffle 111 may be configured to direct fluid away from the mouthpiece portion 112. The baffle 111 may also be configured to knock out larger particles from the exhalation airflow and prevent or reduce particles larger than a virus or pathogen from reaching the porous sample collection media 120. The baffle 111 include one more projection elements that are configured to form a torturous airflow path to knock out larger particles from the exhalation airflow and prevent or reduce particles larger than a virus or pathogen from reaching the porous sample collection media 120.

The metered fluid dose element 140 may be movably attached to the fluid inlet port 130 between a first fluid loaded position and a second fluid depleted position, where the second fluid depleted position is closer to the housing than the first fluid loaded position. In the first fluid loaded position the metered fluid dose element 140 contains the metered volume of fluid and in the second fluid depleted position the metered fluid dose element 140 delivers the metered volume of fluid into the fluid inlet 130 and onto the porous sample collection media 120.

The metered fluid dose element 140 may contain a reservoir of fluid 142. The metered fluid dose element 140 may define a volume configured to retain a reservoir of fluid 142 and release the reservoir of fluid 142 as the metered fluid dose element 140 moved from the first fluid loaded position to the second fluid depleted position. The metered fluid dose element 140 may include a plunger element 145 that moves into the volume configured to retain a reservoir of fluid 142 and release the reservoir of fluid 142 as the metered fluid dose element 140 moved from the first fluid loaded position to the second fluid depleted position. The plunger element 145 may include an aperture 141 to release the fluid release the reservoir of fluid 142 as the metered fluid dose element 140 moved from the first fluid loaded position to the second fluid depleted position. A seal element may cover the aperture 141 and seal the fluid in the reservoir of fluid 142 until pressure or force ruptures the seal, releasing the fluid into the fluid inlet port 130. One illustrative metered fluid dose element 140 is commercially available from 3M Company (St. Paul MN, U.S.A.) under the trade designation CUROS. One illustrative metered fluid dose element 140 is commercially available from 3M Company (St. Paul MN, U.S.A.) under the trade designation CUROS. FIG. 10 illustrates a cross-sectional view of the metered fluid dose element 140. The metered fluid dose element 140 shown in FIGS. 1-6 and 8-9 include these elements illustrated here in the cross-sectional of FIG. 7.

The fluid inlet port 130 may define a protrusion 132 extending away from an outer surface of the housing 110. The metered fluid dose element 140 may define a cap movably attached to the protrusion 132 between the first fluid loaded position and the second fluid depleted position.

The porous sample collection media 120 defines a major surface area value and the fluid reservoir 142 defines a volume value, and the volume value divided by the surface area value may be in a range from 10 microliters/cm2 to 400 microliter/cm2, or from 10 microliters/cm2 to 250 microliter/cm2, or from 50 microliters/cm2 to 150 microliter/cm2. In some embodiments, the fluid reservoir 142 defines a volume in a range from 50 microliters to 500 microliters.

The metered fluid dose element 140 may be movably attached via a threaded connection 134 with the fluid inlet port 130. Thus, the metered fluid dose element 140 may be moved between the first fluid loaded position and the second fluid depleted position by rotating the metered fluid dose element 140 about a threaded axis.

The fluid dispensed by the metered fluid dose element 140 may be any fluid described herein.

The sample collection device 300 may further include a fluid flow channel 118 configured to direct fluid from the fluid inlet port 130 to the porous sample collection media 120. The fluid flow channel 118 may deliver fluid via capillary action to the porous sample collection media 120.

The sample collection device 400 may include a fluid collection receptacle 150 disposed within the housing 110 and configured to receive fluid from the porous sample collection media 120. The sample collection device 400 may further include a second fluid flow channel 119 configured to direct fluid from the porous sample collection media 120. The second fluid flow channel 119 may deliver fluid via capillary action. The fluid collection receptacle 150 may include a fluid outlet 152 configured to direct fluid out of the sample collection device 400.

In some embodiments, the sample collection device 400 may include two, three, four, or five, or more fluid inlet ports 130. Each fluid inlet port 130 may independently include a metered fluid dose element 140 attached to the corresponding fluid inlet port 130. The two or more metered fluid dose elements 140 may each include the same fluid material. Alternatively, at least one of the two or more metered fluid dose elements 140 may include a fluid material that is different than fluid material contained in another metered fluid dose element 140. As described above, the different fluids may be chosen to interact or react with each other upon deployment of each fluid into the sample collection device 400.

The disclosure is also directed to a sample collection system. The sample collection system includes the sample collection device 400 described above and an assay configured to receive fluid from the fluid collection receptacle 150 via the fluid outlet 152, as described above.

Figure 11:
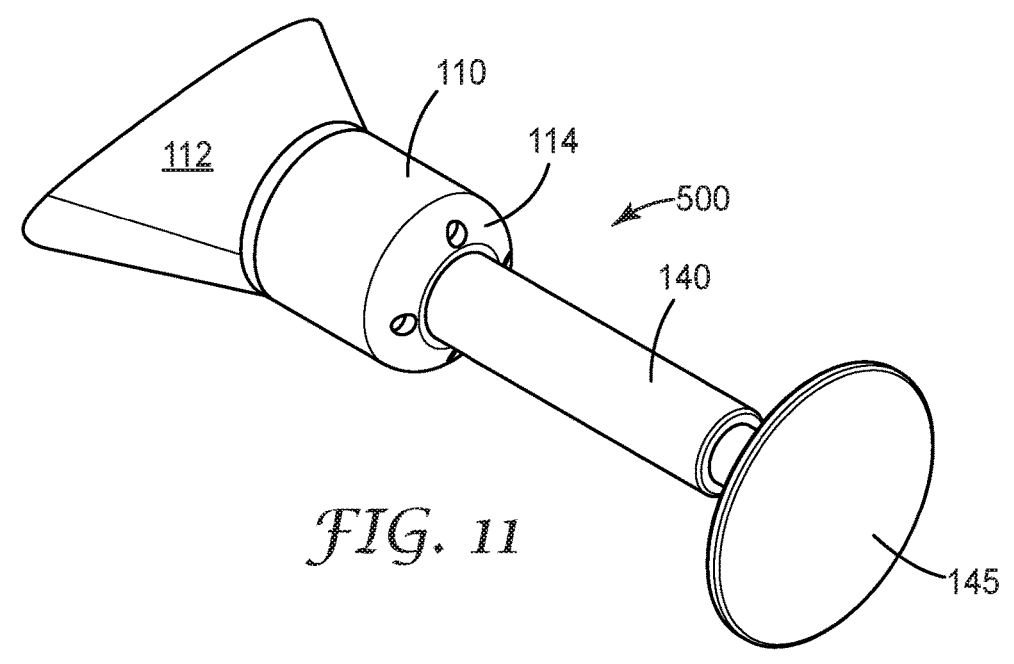
FIG. 11 is a rear perspective schematic diagram of another illustrative sample collection device with a detachable mouthpiece.
Figure 12:
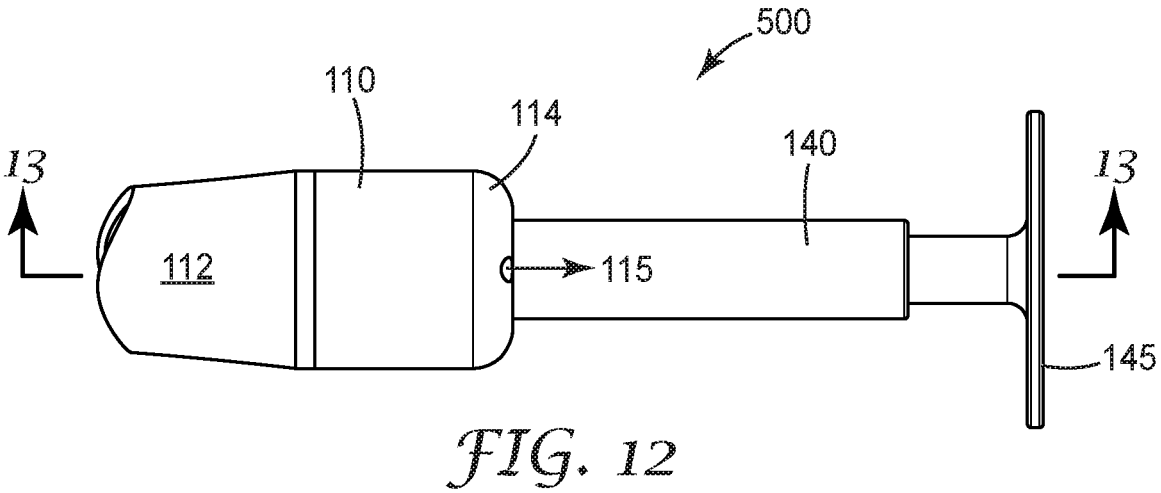
FIG. 12 is a side elevation schematic diagram of the sample collection device of FIG. 11.
Figure 13:
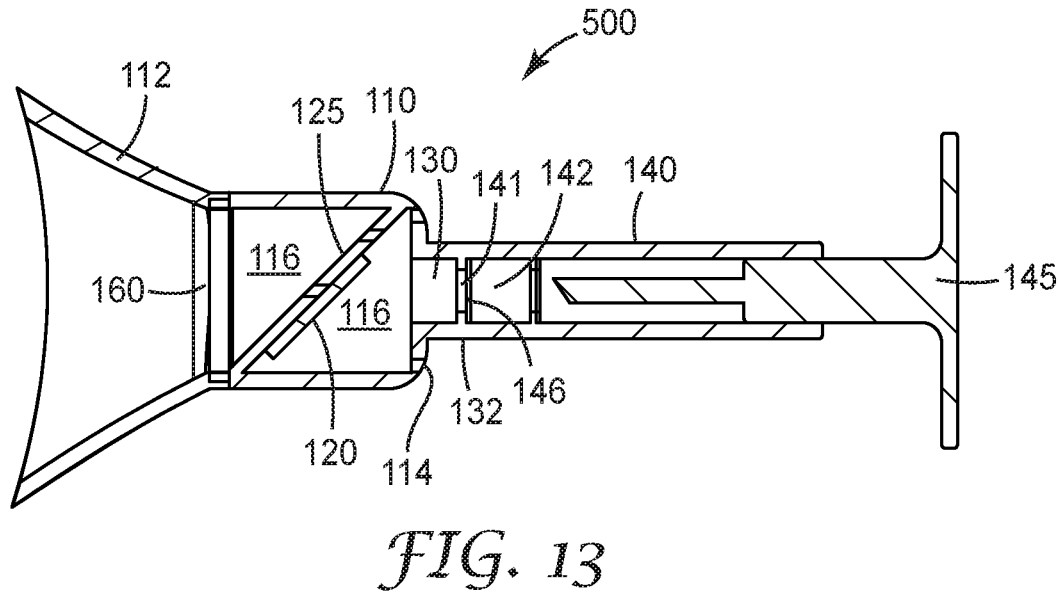
FIG. 13 is a cross-sectional schematic diagram of the sample collection device of FIG. 12.
Figure 14:
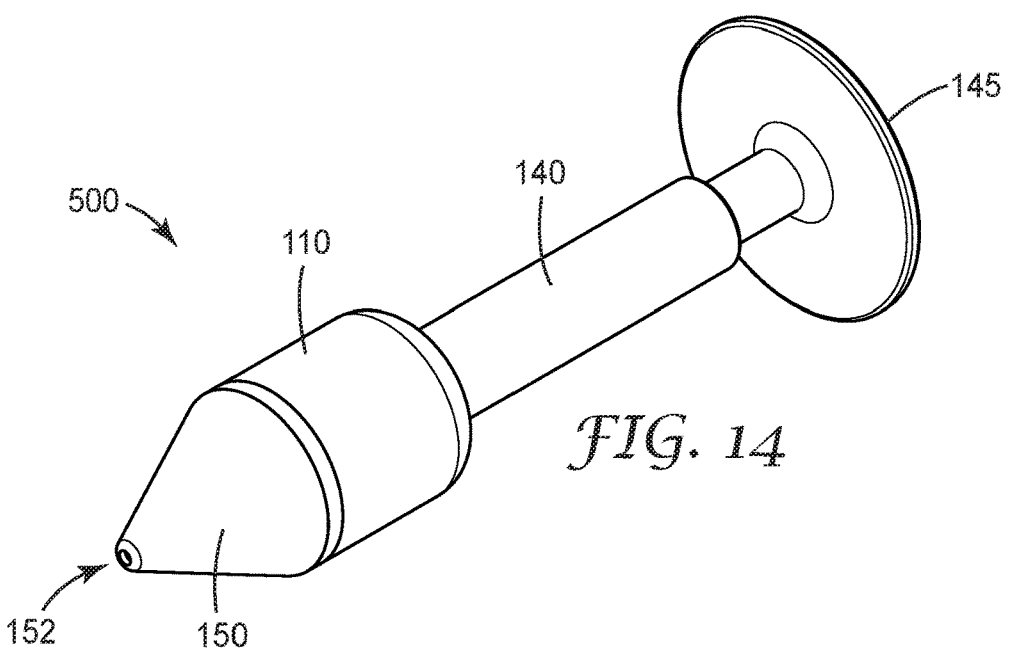
FIG. 14 is a rear perspective schematic diagram of another illustrative sample collection device with a detachable fluid collection receptacle.
Figure 15:
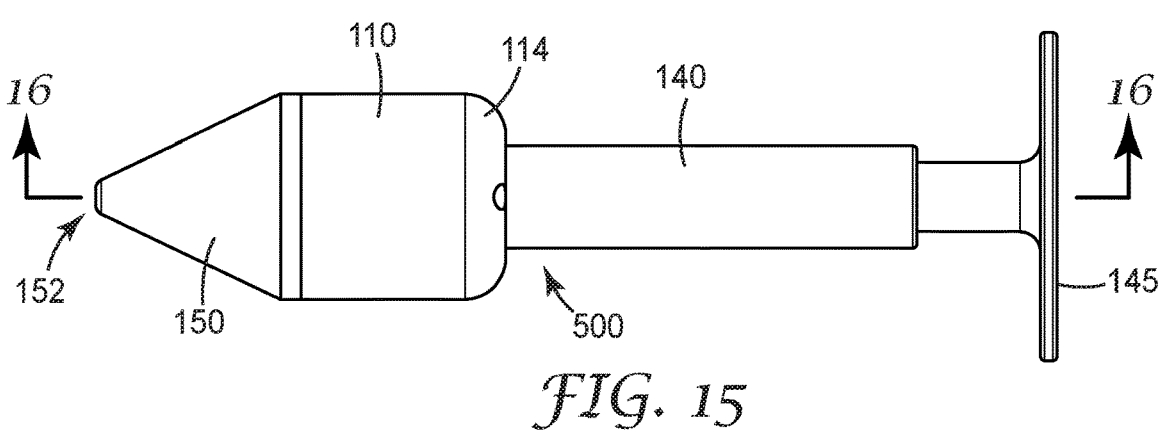
FIG. 15 is a side elevation schematic diagram of the sample collection device of FIG. 14.
Figure 16:
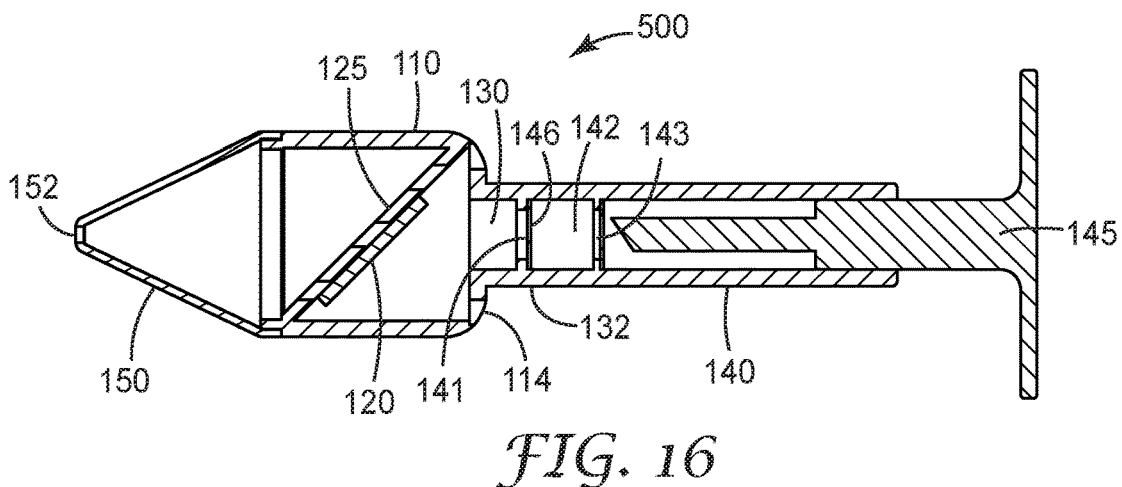
FIG. 16 is a cross-sectional schematic diagram of the sample collection device of FIG. 15.

FIG. 11 is a rear perspective schematic diagram of another illustrative sample collection device 500 with a detachable mouthpiece. FIG. 12 is a side elevation schematic diagram of the sample collection device 500 of FIG. 11. FIG. 13 is a cross-sectional schematic diagram of the sample collection device 500 of FIG. 12. FIG. 14 is a rear perspective schematic diagram of another illustrative sample collection device 500 with a detachable fluid collection receptacle. FIG. 15 is a side elevation schematic diagram of the sample collection device 500 of FIG. 14. FIG. 16 is a cross-sectional schematic diagram of the sample collection device 500 of FIG. 15.

FIG. 11 to FIG. 15 is the same sample collection device 500 except for an interchangeable mouthpiece portion 112 and fluid collection receptacle 150. A user would exhale into the mouthpiece portion 112 of the sample collection device 500 and then replace the mouthpiece portion 112 with the fluid collection receptacle 150 and release the fluid for collection by the fluid collection receptacle 150 and subsequent testing, as described above.

The sample collection device 500 including a housing 110 extending from a mouthpiece portion 112 to an air outlet portion 114. The housing 110 defines an airflow channel 116 from the mouthpiece portion 112 to the air outlet portion 114. The mouthpiece portion 112 is configured to receive an exhalation airflow 115. A porous sample collection media 120 is disposed within the housing 110 and along the airflow channel 116. A fluid inlet port 130 defines an aperture through the housing 110 and is adjacent to the porous sample collection media 120. The fluid inlet port 130 is configured to direct fluid onto the porous sample collection media 120. A metered fluid dose element 140 is movably attached to the fluid inlet port 130. The metered fluid dose element 140 is configured to dispense a metered volume of fluid into the fluid inlet port 130.

The housing 110 may be formed of a rigid material, such as plastic. The airflow channel 116 may extend from a mouthpiece portion 112 opening to an air outlet portion 114 having one or more air outlets. A user exhales into the mouthpiece portion 112 opening and the exhalation airflow leaves the sample collection device 500 through the one or more air outlets at the air outlet portion 114. The airflow channel 116 may extend longitudinally along a longitudinal axis of the housing 110. The airflow channel 116 may extend co-axially along a central longitudinal axis of the housing 110.

The porous sample collection media 120 is disposed within the housing 110 and along the airflow channel 116. Exhalation airflow 115 passes through the thickness of the porous sample collection media 120. The porous sample collection media 120 at least partially occludes the airflow channel 116. The porous sample collection media 120 may occlude the airflow channel 116. The porous sample collection media 120 may have a major plane that is orthogonal to the direction of the exhalation airflow 115 passing through the thickness of the porous sample collection media 120.

The porous sample collection media 120 is shown having a major plane that forms an angle with the direction of the incident exhalation airflow 115 passing through the thickness of the porous sample collection media 120. This angle may be in a range from about 91 degrees to about 179 degrees, or from about 100 degrees to about 160 degrees, or about 115 degrees to about 150 degrees, or about 125 to about 145 degrees.

The porous sample collection media 120 may be formed of any material described herein.

The porous sample collection media 120 may be fixed directly to the housing 110. FIG. 13 and FIG. 16 show a support element 125 in contact with and supporting the porous sample collection media 120. The support element 125 includes one or more apertures configured to allow exhalation airflow to pass through the support element 125. The support element 125 may be fixed to the housing 110 and disposed within the airflow channel 116. The porous sample collection media 120 may be fixed directly to the support element 125.

The metered fluid dose element 140 may include a plunger element 145 movably attached to the fluid inlet port 130 between a first fluid loaded position and a second fluid depleted position, where the second fluid depleted position is closer to the housing than the first fluid loaded position. In the first fluid loaded position the metered fluid dose element 140 contains the metered volume of fluid and in the second fluid depleted position the metered fluid dose element 140 delivers the metered volume of fluid into the fluid inlet 130 and onto the porous sample collection media 120.

The metered fluid dose element 140 may contain a reservoir of fluid 142. The metered fluid dose element 140 may define a volume configured to retain a reservoir of fluid 142 and release the reservoir of fluid 142 as the metered fluid dose element 140 moved from the first fluid loaded position to the second fluid depleted position. The metered fluid dose element 140 may include a plunger element 145 that moves into the volume configured to retain a reservoir of fluid 142 and release the reservoir of fluid 142 as the metered fluid dose element 140 moved from the first fluid loaded position to the second fluid depleted position. FIG. 13 and FIG. 16 illustrate a cross-sectional view of the metered fluid dose element 140. The reservoir of fluid 142 may include a first seal 143 and a second seal 146 to contain the fluid within the reservoir of fluid 142. The plunger 145 may pierce the first seal 143 and form an apertures 141 in the second seal 146 to release the fluid into the fluid inlet port 130.

The fluid inlet port 130 may define a protrusion 132 extending away from an outer surface of the housing 110. The metered fluid dose element 140 may include a plunger element 145 movably attached to the protrusion 132 between, at least, the first fluid loaded position and the second fluid depleted position.

The porous sample collection media 120 defines a major surface area value and the fluid reservoir 142 defines a volume value, and the volume value divided by the surface area value may be in a range from 10 microliters/cm2 to 400 microliter/cm2, or from 10 microliters/cm2 to 250 microliter/cm2, or from 50 microliters/cm2 to 150 microliter/cm2. In some embodiments, the fluid reservoir 142 defines a volume in a range from 50 microliters to 500 microliters.

The fluid dispensed by the metered fluid dose element 140 may be any fluid described herein.

The sample collection device 500 may include a pre-filter element 160 fixed within the mouthpiece 112 and along the airflow channel 116. Alternatively, the pre-filter element 160 may be located between the mouthpiece element 112 and the porous sample collection media 120 along the airflow channel 116. Exhalation airflow 115 passes through the thickness of the pre-filter element 160. The pre-filter element 160 at least partially occludes the airflow channel 116. The pre-filter element 160 may occlude the airflow channel 116.

The pre-filter element 160 is illustrated as having a major plane that is orthogonal to the direction of the exhalation airflow 115 passing through the thickness of the pre-filter element 160. The pre-filter element 160 may be a non-woven layer configured to filter out larger particles from the exhalation airflow 115 passing through the pre-filter element 160. The pre-filter element 160 may be a non-woven layer that does not have an electrostatic charge. The pre-filter element 160 is configured to not capture virus or pathogens. The pre-filter element 160 is configured to allow virus or pathogens to transmit through the pre-filter element 160. The pre-filter element 160 may be incorporated into any of the embodiments illustrated herein.

The sample collection device 500 may further include a fluid flow channel configured to direct fluid from the fluid inlet port 130 to the porous sample collection media 120. The fluid flow channel may deliver fluid via capillary action to the porous sample collection media 120.

The sample collection device 500 may include a fluid collection receptacle 150 disposed within the body 110 and configured to receive fluid from the porous sample collection media 120. The sample collection device 500 may further include a second fluid flow channel configured to direct fluid from the porous sample collection media 120. The second fluid flow channel may deliver fluid via capillary action. The fluid collection receptacle 150 may include a fluid outlet 152 configured to direct fluid out of the sample collection device 500.

In some embodiments, the sample collection device 500 may include two, three, four, or five, or more fluid inlet ports 130. Each fluid inlet port 130 may independently include a metered fluid dose element 140 movably attached to the corresponding fluid inlet port 130. The two or more metered fluid dose elements 140 may each include the same fluid material. Alternatively, at least one of the two or more metered fluid dose elements 140 may include a fluid material that is different than fluid material contained in another metered fluid dose element 140. As described above, the different fluids may be chosen to interact or react with each other upon deployment of each fluid into the sample collection device 500.

The disclosure is also directed to a sample collection system. The sample collection system includes the sample collection device 500 described above and an assay config-ured to receive fluid from the fluid collection receptacle 150 via the fluid outlet 152.

All references and publications cited herein are expressly incorporated herein by reference in their entirety into this disclosure, except to the extent they may directly contradict this disclosure. Although specific embodiments have been illustrated and described herein, it will be appreciated by those of ordinary skill in the art that a variety of alternate and/or equivalent implementations can be substituted for the specific embodiments shown and described without depart-ing from the scope of the present disclosure. It should be understood that this disclosure is not intended to be unduly limited by the illustrative embodiments and examples set forth herein and that such examples and embodiments are presented by way of example only with the scope of the disclosure intended to be limited only by the claims set forth here.

The invention claimed is:

1. A sample collection device comprising:
a housing extending from an exhalation receipt portion to an air outlet portion, the housing defining an airflow channel from the exhalation receipt portion to the air outlet portion, the exhalation receipt portion configured to receive an exhalation airflow;
a porous sample collection media disposed within the housing and along the airflow channel, wherein the porous sample collection media comprises a nonwo-ven material having an electrostatic charge;
a fluid inlet port defines an aperture through the hous-ing and adjacent to the porous sample collection media, the fluid inlet port configured to direct fluid onto the porous sample collection media; and
a metered fluid dose element attached to the fluid inlet port, the metered fluid dose element configured to dispense a metered volume of fluid into the fluid inlet port.

2. The sample collection device according to claim 1, further comprising a fluid collection receptacle disposed within the housing and configured to receive fluid from the porous sample collection media.

3. The sample collection device according to claim 1, wherein the metered fluid dose element is movably attached to the fluid inlet port between at least a first fluid loaded position and a second fluid depleted position, wherein the second position is closer to the housing than the first position.

4. The sample collection device according to claim 3 wherein the fluid inlet port comprises a protrusion extending away from an outer surface of the housing, and the metered fluid dose element defines a cap attached to the protrusion.

5. The sample collection device according to claim 3, wherein metered fluid dose element delivers fluid to the fluid inlet port when moved from the first position to the second position.

6. The sample collection device according to claim 1, wherein the metered fluid dose element contains a fluid reservoir of fluid.

7. The sample collection device according to claim 6, wherein the porous sample collection media defines a sur-face area value and the fluid reservoir defines a volume value, and the volume value divided by the surface area value is in a range from about 10 microliters/cm$^2$ to about 400 microliter/cm$^2$.

8. The sample collection device according to claim 6, wherein the fluid reservoir defines a volume in a range from about 50 microliters to about 500 microliters.

9. The sample collection device according to claim 1, wherein the metered fluid dose element is movably attached via a threaded connection with the fluid inlet port.

10. The sample collection device according to claim 1, wherein the nonwoven material is hydrophobic.

11. The sample collection device according to claim 1, wherein a fluid used in the sample collection device is at least one of an aqueous fluid, an aqueous buffer solution, an aqueous fluid including a surfactant, a saline solution, or a saline solution including a surfactant.

12. The sample collection device according to claim 1, further comprising a fluid flow channel configured to direct fluid from the fluid inlet port to the porous sample collection media.

13. The sample collection device according to claim 12, the fluid flow channel delivers fluid via capillary action.

14. The sample collection device according to claim 1, further comprising a second fluid flow channel configured to direct fluid from the porous sample collection media.

15. The sample collection device according to claim 14, the second fluid flow channel delivers fluid via capillary action.

16. The sample collection device according to claim 1, wherein exhalation airflow transmits through the porous sample collection media.

17. The sample collection device according to claim 1, comprising two or more inlet ports, and each inlet port independently comprises a metered fluid dose element mov-ably attached to a corresponding fluid inlet port.

18. A sample collection system comprising:
the sample collection device of claim 1; and
an assay configured to receive fluid from the sample collection device.

19. A method comprising:
flowing exhalation air through a porous sample collection media, wherein the porous sample collection media is disposed in an airflow channel forming a loaded porous sample collection media;
flowing a metered dose of fluid through the loaded porous sample collection media disposed in the airflow chan-nel forming an eluent, wherein the porous sample collection media comprises a nonwoven material hav-ing an electrostatic charge;
collecting the eluent.

* * * * *